US012637371B2

(12) United States Patent
Ching

(10) Patent No.: US 12,637,371 B2
(45) Date of Patent: *May 26, 2026

(54) METHOD AND DEVICE FOR CAPTURING AND DISINFECTING CONTAMINANTS FOR DRAINAGE SYSTEM

(71) Applicant: Wing Han Ching, Hong Kong (HK)

(72) Inventor: Wing Han Ching, Hong Kong (HK)

( * ) Notice: Subject to any disclaimer, the term of this patent is extended or adjusted under 35 U.S.C. 154(b) by 685 days.

This patent is subject to a terminal disclaimer.

(21) Appl. No.: 18/073,565

(22) Filed: Dec. 2, 2022

(65) Prior Publication Data

US 2023/0097063 A1     Mar. 30, 2023

Related U.S. Application Data

(63) Continuation-in-part of application No. 17/528,216, filed on Nov. 17, 2021, now Pat. No. 11,541,146.

(30) Foreign Application Priority Data

Feb. 7, 2021     (CN) .......................... 202110174867.9

(51) Int. Cl.
| | |
|---|---|
| *C02F 1/72* | (2023.01) |
| *A61L 9/014* | (2006.01) |
| *B01D 53/88* | (2006.01) |

(52) U.S. Cl.
CPC .............. *C02F 1/725* (2013.01); *A61L 9/014* (2013.01); *B01D 53/885* (2013.01);
(Continued)

(58) Field of Classification Search
CPC ...... C02F 1/725; C02F 2303/04; A61L 9/014; A61L 2209/15; B01D 53/885; B01D 2257/91; B01D 2258/06
See application file for complete search history.

(56) References Cited

U.S. PATENT DOCUMENTS

| | | | | |
|---|---|---|---|---|
| 5,997,733 A | * | 12/1999 | Wilbur | .................... A61L 11/00 210/85 |
| 10,786,592 B2 | | 9/2020 | Keith | |

(Continued)

FOREIGN PATENT DOCUMENTS

| | | |
|---|---|---|
| CN | 202466793 U | 10/2012 |
| CN | 105999352 A | 10/2016 |

(Continued)

*Primary Examiner* — Brendan A Hensel
(74) *Attorney, Agent, or Firm* — IDEA Intellectual Limited; Sam T. Yip

(57) ABSTRACT

A method for removing contaminants from exhaust air and liquid using a disinfection device comprising a housing having a chamber and a top end. The chamber has a body and a reducing part. The reducing part comprises a first opening at the bottom end of the chamber and a floating body configured to seal the first opening at the bottom end. The disinfection device further comprises a spiral guiding channel having an inlet and an outlet connecting to the chamber; and an exhaust conduit having an expandable part at one end of the exhaust conduit. The exhaust conduit connects to the top end of the housing and partially extends through the body of the chamber. A nonluminous disinfection part is installed in the disinfection device interior so as to remove air contaminants when air is passing through the chamber from the spiral guiding channel to the exhaust conduit.

11 Claims, 2 Drawing Sheets

100

(52) U.S. Cl.
CPC ....... *A61L 2209/15* (2013.01); *B01D 2257/91*
(2013.01); *C02F 2303/04* (2013.01)

(56) References Cited

U.S. PATENT DOCUMENTS

| | | | |
|---|---|---|---|
| 11,541,146 B2 * | 1/2023 | Ching | ................ B01D 53/8668 |
| 2017/0080373 A1 | 3/2017 | Engelhard | |

FOREIGN PATENT DOCUMENTS

| | | | |
|---|---|---|---|
| CN | 210984221 U | 7/2020 | |
| CN | 211499038 U | 9/2020 | |
| DE | 102005036580 A1 | 3/2007 | |
| KR | 200426286 Y1 * | 9/2006 | ........... B01D 53/885 |

* cited by examiner

100

METHOD AND DEVICE FOR CAPTURING AND DISINFECTING CONTAMINANTS FOR DRAINAGE SYSTEM

CROSS-REFERENCE TO RELATED APPLICATIONS

The present application is a continuation-in-part of U.S. patent application Ser. No. 17/528,216 filed Nov. 17, 2021; the disclosure of which is incorporated herein by reference in its entirety.

FIELD OF THE INVENTION

The present invention provides a disinfection device and method for disinfecting contaminants for the drainage system. More specifically, the disinfection device is able to capture and disinfect the contaminants of the exhaust air when the exhaust air passing through the chamber of the disinfection device from the spiral guiding channel to the exhaust conduit or vice versa.

BACKGROUND

Often liquid waste and excreta produced from a residential property is discharged by its drainage system. More specifically, the drainage system includes branch pipes and main vertical drainage pipes, where the branch pipes are configured to collect the waste from sanitary fitments in each flat of each floor, then followed by gathering to the main drainage pipes. When infectious pollutants are discharged from one of the properties, the infectious aerosols thereof are released and spread to the surrounding areas from the opening of drainage pipes located on the rooftop of the building through the interconnected drainage pipes. This could negatively impact nearby residents.

The outbreak of SARS in the Amoy Gardens in Hong Kong SAR in 2003 and similar transmission route of COVID-19 at the Fu Heng Estate in the same city in 2020 were all related to the design of the existing drainage system. Specifically, in regard to the incident at Fu Heng Estate, a resident of unit 13 on the $32^{nd}$ floor was earlier confirmed to be infected with COVID-19. The drainage pipe of unit 13 terminated on the rooftop of the building and was located opposite to unit 14. Infected aerosol was suspected to have discharged from the open end of the drainage pipe on the rooftop of the building and transmitted to unit 14 on the $34^{th}$ floor, the top floor of the building, by wind wake effect.

In view of the disadvantages of the existing drainage system, there is a need for providing a disinfection device and method adaptable to existing drainage systems so as to eliminate or reduce the potential transmission of infected aerosol or contaminants from the open end of the drainage pipe.

SUMMARY OF THE INVENTION

A first aspect of the present invention provides a method for removing contaminants from exhaust air using a disinfection device. The disinfection device includes a housing having a chamber and at least a top end. The chamber has a body and a reducing part, and the reducing part includes an opening at a bottom end of the chamber and a floating body configured to seal the opening at the bottom end. A spiral guiding channel has an inlet and an outlet. The spiral guiding channel is adjacent to an exterior wall of the housing and connected to the outlet of the chamber.

The disinfection device further includes an exhaust conduit, which includes an expandable part at one end of the exhaust conduit and a disinfection part installed in the interior of the disinfection device. The spiral guiding channel is adjacent to the exterior wall of the housing and connected to the chamber through the outlet. Further, the exhaust conduit positioned in the chamber connected to the top end of the housing and partially extends through the body of the chamber. Therefore, the configuration of the spiral guiding channel, chamber, and the exhaust conduit would not block the air pathway, and the air flow in and out freely to the drainage system.

Moreover, the disinfection part is installed on an interior wall of the body of the chamber for removing air contaminants from air passing through the chamber from the spiral guiding channel to the exhaust conduit.

The method for removing contaminants from exhaust air includes guiding the exhaust air having contaminants through the spiral guiding channel to the chamber; disinfecting the exhaust air by the disinfection part configured for removing the contaminants when the exhaust air passing through the body of the chamber producing a sterile air; and discharging the sterile air through the exhaust conduit.

In one embodiment of the first aspect of the present invention, the spiral guiding channel is connected to the chamber such that exhaust air flows from the spiral guiding channel to the chamber and the contaminants are captured and removed by the disinfection part of the chamber.

In one embodiment of the first aspect of the present invention, the housing further includes a clamping part extended from the housing so as to mount the disinfection device on a drainage system.

In one embodiment of the first aspect of the present invention, the disinfection part further includes a catalyst layer or disinfectant coating positioned on the interior wall of the chamber.

A second aspect of the present invention provides a method for removing contaminants from mixture of liquid and exhaust air using a disinfection device having a housing, a spiral guiding channel, an exhaust conduit, and a disinfection part. The housing includes a chamber and a top end, the chamber has a body and a reducing part. The reducing part has an opening at a bottom end of the chamber and a floating body configured to seal the opening at the bottom end. The spiral guiding channel is external to the chamber and has an inlet and an outlet. The spiral guiding channel is adjacent to an exterior wall of the housing and connected to the outlet of the chamber. The exhaust conduit has an expandable part at one end of the exhaust conduit, and the exhaust conduit is coupled to the top end of the housing and partially extending through the body of the chamber. The disinfection part is installed on an interior wall of the body of the chamber.

The method includes: (1) guiding the mixture of liquid and exhaust air through the exhaust conduit, the exhaust conduit connecting and extending into the chamber; (2) disinfecting the mixture of liquid and exhaust air by the disinfection part configured for removing the contaminants when the mixture of liquid and exhaust air passing through the body of the chamber producing a sterile air and a sterile liquid; (3) discharging the sterile air through a spiral guiding channel; (4) accumulating the sterile liquid at the reducing part including a first opening at the bottom end of the chamber and a floating body configured to seal the first opening at the bottom end of the chamber; and (5) discharging the sterile liquid through the opening at the bottom end of the chamber to the drainage system. Moreover, the liquid is accumulated at the bottom end of the chamber due to the block of the floating body, and once the buoyancy is greater than the weight of the floating body, the liquid is discharged through the opening at the bottom end of the chamber.

In one embodiment of the second aspect of the present invention, the density of the floating body is lower than the density of the liquid.

In one embodiment of the second aspect of the present invention, the exhaust conduit guides the mixture of liquid and exhaust air to the chamber and the contaminants are captured and removed by the disinfection part.

In one embodiment of the second aspect of the present invention, the housing further includes a clamping part configured for mounting the disinfection device on a drainage system.

In one embodiment of the second aspect of the present invention, the disinfection part further includes a catalyst layer or disinfectant coating.

A third aspect of the present invention provides an apparatus for removing one or more contaminants using a disinfection device. The apparatus includes a housing. The housing includes a top end, a clamping part mounting a drainage system to the disinfection device, and a chamber. The chamber includes a body, a reducing part, and a non-luminous disinfection part. The reducing part comprises an opening at a bottom end of the chamber and a floating body configured to seal the opening at the bottom end. The nonluminous disinfection part includes a catalyst layer or any disinfectant coating configured for removing the contaminants on an interior wall of the body of the chamber. The apparatus further includes a spiral guiding channel externally coupled to the chamber of the housing. The spiral guiding channel includes an inlet and an outlet. The spiral guiding channel is set along a tangent plane of the housing. The apparatus further includes an exhaust conduit coupled to the top end of the housing and partially extending through the body of the chamber. The exhaust conduit has an expandable part positioned in the chamber. The expandable part includes a first opening and a second opening. The first opening has a cross-sectional area smaller than a cross-sectional area of the second opening.

In one embodiment of the third aspect of the present invention, the housing further includes a cover positioned on the top end of the housing.

In one embodiment of the third aspect of the present invention, the cross-sectional area of the exhaust conduit is equal to or slightly larger than the cross-sectional area of the top opening of the expandable part.

In one embodiment of the third aspect of the present invention, where the size of the floating body is greater than the aperture of the first opening of the bottom end of the chamber.

In one embodiment of the third aspect of the present invention, the reducing part is located directly under the exhaust conduit. The cross-sectional area of the expandable part is increased along a direction from the exhaust conduit toward the reducing part, and the cross-sectional area of the reducing part is decreased along the direction.

In one embodiment of the third aspect of the present invention, at least one chamber channel, adjacent to the exhaust conduit of the chamber, is collectively defined by the interior wall of the body.

In one embodiment of the third aspect of the present invention, the chamber channel communicates with the spiral guiding channel through the outlet of the spiral guiding channel. The spiral guiding channel makes a turn adjacent to the top end of the housing, such that a flowing direction of air in the spiral guiding channel is opposite to a flowing direction of air in the chamber channel.

In one embodiment of the third aspect of the present invention, the chamber channel further includes a first chamber channel and a second chamber channel located at two opposite sides of the exhaust conduit.

BRIEF DESCRIPTION OF THE DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

DETAILED DESCRIPTION

Figure 1:
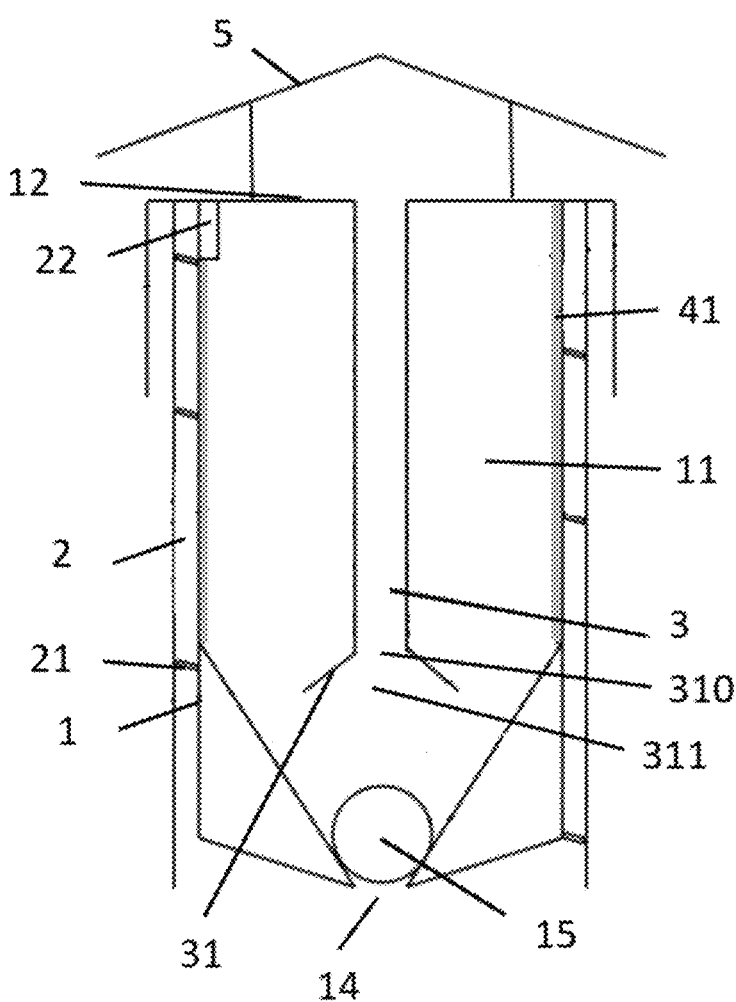
FIG. 1 depicts a side cross-sectional view of the disinfection device in one embodiment of the present invention.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of preparation described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step 1, Step 2, Step 3, Step 4, and Step 5" shall be construed to mean step 1 is carried out first, step 5 is carried out last, and steps 2, 3, and 4 can be carried out in any sequence between steps 1 and 5, and that the sequence still falls within the literal scope of the claimed process. A given step or sub-set of steps can also be repeated.

In the following description, the present disinfection devices are set forth as preferred examples. It will be apparent to those skilled in the art that modifications, including additions and/or substitutions may be made without departing from the scope and the spirit of the invention. Specific details may be omitted so as not to obscure the invention; however, the disclosure is written to enable one skilled in the art to practice the teachings herein without undue experimentation.

The present invention provides a method of providing a disinfection device for removing contaminants or infected aerosol from exhaust air and a mixture of liquid and exhaust air in order to sterilize thereof without ultraviolet light or other visible light. More specifically, the disinfection device includes a housing having a chamber and at least a top end, a spiral guiding channel having an inlet and an outlet, an exhaust conduit having an expandable part at one end of the exhaust conduit and a nonluminous disinfection part installed in the interior of the disinfection device. The spiral guiding channel is adjacent to the exterior wall of the housing and connected to the chamber through the outlet. In addition, the disinfection device further includes a clamping part such that the disinfection device in the present invention is able to be mounted at the edge of an opening of the draining pipe. The spiral guiding channel is connected to the chamber and is utilized to accelerate the flow of the exhaust air before entering into the chamber when the drainage system is in positive pressure. Due to the cyclonic effect, the relatively heavier infected aerosol or contaminants will land on the inner surface of the chamber and be disinfected or sterilized by the nonluminous disinfection part equipped with a catalyst layer when the catalyst is activated. Then, the disinfected air will be discharged to the atmosphere through the exhaust conduit connecting to the top end of the housing.

Alternatively, the present invention provides a method for removing contaminants from exhaust air of a drainage system, which includes following steps: (1) the exhaust air having contaminants flows through the spiral guiding channel 2 into the device 100; (2) the contaminants of the exhaust air are absorbed on the inner surface of the chamber 11 due to the centrifugal force and then disinfected by the disinfection part 41 fixed on the inner surface of the chamber 11 producing a sterile air; (3) the sterile air is discharged to the atmosphere through the exhaust conduit 3.

Alternatively, the present invention provides a method for removing contaminants from a mixture of liquid and exhaust air of a drainage system, which includes following steps: (1) the mixture of the liquid and exhaust air having contaminants flow through the exhaust conduit 3 into the device 100; (2) the contaminants of the exhaust air are absorbed on the inner surface of the chamber 11 and then disinfected by the disinfection part 41 fixed on the inner surface of the chamber 11 producing a sterile air and a sterile liquid; (3) the sterile air is discharged to the drainage pipe 6 through the spiral guiding channel 2; (4) the sterile liquid accumulates at the bottom end of the chamber 11 where a floating body 15 is configured to block the opening 14 at the bottom end of the chamber; (5) the sterile liquid is discharged through the opening 14 at the bottom end of the chamber 11 to the drainage pipe 6. The aforementioned methods may significantly reduce or eliminate the emission of infectious aerosol in the main drainage pipe so as to avoid the impact of the infectious aerosol on the environment and reduce the impact on the lives of surrounding residents.

The chamber further includes a body and a reducing part, where the reducing part includes a first opening at the bottom end of the chamber and a floating body configured to seal the first opening at said bottom end. When the drainage system is in negative pressure, the air from the atmosphere enters into the drainage system along a pressure gradient through the disinfection device in the present invention. In case where there is rain water entering into the disinfection device and accumulating at the reducing part of the chamber of the disinfection device, the floating body will float up and allow the liquid to be discharged to the drainage system once the buoyancy of the floating body is over the weight thereof. Once the liquid is discharged, the floating body will return to its initial position and seal the first opening at the bottom end of the chamber so as to stop the infected aerosol bypassing the body of the chamber and releasing to the atmosphere.

Figure 2:
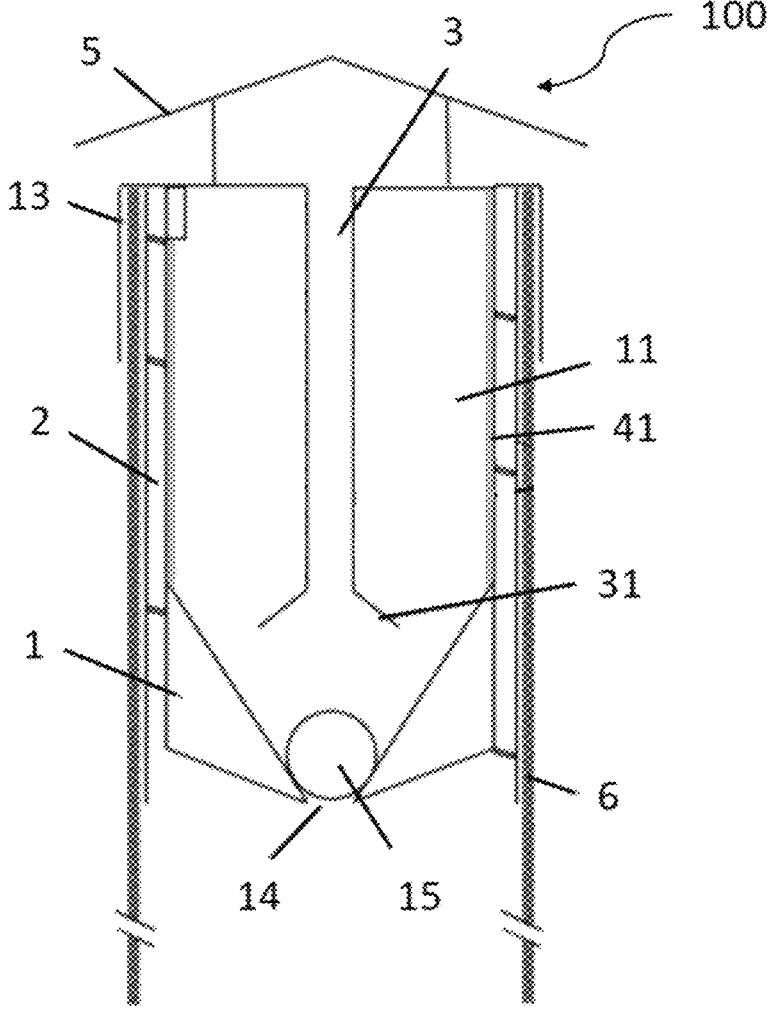
FIG. 2 depicts the disinfection device of one embodiment of the present invention being installed to a typical drainage pipe.

FIG. 1 illustrates a cross-sectional view of the capture and disinfected device 100 in one embodiment of the present invention (hereinafter as "the device"). The device 100 includes a housing 1 having a chamber 11 and a top end 12, a spiral guiding channel 2 having an inlet 21 and an outlet 22, an exhaust conduit 3 having an expandable part 31 at one end of the exhaust conduit and a disinfection part 41 installed in an interior of the device 100. The spiral guiding channel 2 is adjacent to an exterior wall of the housing 1 and connected to the chamber 11 through the outlet 22. In one embodiment of the present invention, the housing 1 further includes a clamping part 13 to mount the device 100 on the drainage pipe 6 of the drainage system as shown in FIG. 2. In another embodiment of the present invention, the clamping part 13 is further provided with a groove where an opening of the groove is facing downward of the housing 1. The opening of the groove can be clamped on an interior wall of the drainage pipe 6 to make the housing 1 stay more steadily on the drainage system. Preferably, to avoid gas leakage, the groove further includes a sealing gasket between the housing 1 and the interior wall of the drainage pipe 6. The clamping part 13 is detachable from the drainage pipe 6.

When the drainage system is in positive pressure, the exhaust air with infected aerosol or contaminants flows into the device 100 from the inlet 21 of the spiral guiding channel to the chamber 11. Before entering into the chamber 11, the exhaust air will be accelerated and span several times by the spiral guiding channel 2. Due to the cyclonic effect, the relatively heavier infected aerosol and contaminants will land on the inner surface of the chamber 11. Preferably, the cross-sectional area of the spiral guiding channel 2 decreases from the inlet 21 to the outlet 22 so as to increase the flow speed of the exhaust air when flowing through the spiral guiding channel 2 and entering into the chamber 11. The increase in the flow speed of the exhaust air will enforce the centrifugal force to the infected aerosol or contaminants in the exhaust air, such that the infected aerosol or contaminants can more easily adhere to the inner surface of the chamber 11. Preferably, the housing 1 is in a cylindrical shape and the outlet 22 of the spiral guiding channel 2 is set along the tangent plane of the housing 1, such that the gas is able to perform a circular movement along the inner surface of the chamber 11 to improve the adhesion effect of aerosol in the gas.

In another embodiment of the present invention, the disinfection part 41 is nonluminous and it further includes a catalyst layer 41 or a disinfectant coating 41. The catalyst layer 41 produces active oxygen under the activation without ultraviolet light or other visible light. The catalyst layer or the disinfectant coating does not need UV light to activate the disinfection process. As such, the disinfection part is able to effectively reduce the emission of infectious aerosol and contaminants disperse to the atmosphere even without using an ultraviolet lamp.

In another embodiment of the present invention, the expandable part 31 of the exhaust conduit 3 includes a top opening 310 and a bottom opening 311 wherein the cross-sectional area of the bottom opening 311 is larger than the cross-sectional area of the top opening 310. The expandable part 31 can reduce the speed of the air flow in the chamber 11 so as to avoid the adsorbed aerosol on the inner surface of the chamber 11 being dissolved and aerosolized again and then discharged into the atmosphere through the exhaust conduit 3.

When the drainage system is in negative pressure, air from the atmosphere flows into the drainage pipe 6 through the device 100 of the present invention along a pressure gradient. More specifically, the air will flow from the exhaust conduit 3 into the chamber 11, then to the drainage pipe 6 through the spiral guiding channel 2 as shown in FIG. 2. Meanwhile, the air is also disinfected or sterilized when flowing through the nonluminous disinfection part 41 in the chamber 11 so as to keep the incoming air to the drainage system disinfected.

In another embodiment of the present invention, the device 100 further includes a cover 5 positioned on the top end 12 of the housing to reduce the liquid entering into the device 100 directly. The liquid initially accumulates at the bottom end of the chamber due to the blockage of the floating body 15. When the liquid reaches a level that the liquid density is higher than that of the floating body 15, the floating body 15 will float and the opening 14 will be unblocked, such that the accumulated liquid is discharged to the drainage pipe 6 through the opening 14 at the bottom end of the chamber. After the discharge of the liquid, the floating body 15 will return to the original position to block the opening 14 at the bottom end of the chamber so as to avoid the gas from the drainage pipe 6 bypassing into the chamber 11. Preferably, the structure of the bottom of the chamber is formed as a reducing part, but not limited to a reverse conical structure so as to improve the liquid collection efficiency.

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. A method for removing one or more contaminants from exhaust air using a disinfection device comprising a housing, a spiral guiding channel, an exhaust conduit, and a disinfection part, wherein the housing comprises a chamber and a top end, the chamber has a body and a reducing part, wherein the reducing part comprises an opening at a bottom end of the chamber and a floating body configured to seal the opening at the bottom end;

wherein the spiral guiding channel is external to the chamber and having an inlet and an outlet, the spiral guiding channel is adjacent to an exterior wall of the housing and connected to the outlet of the chamber;

wherein the exhaust conduit has an expandable part at one end of the exhaust conduit, the exhaust conduit is coupled to the top end of the housing and partially extending through the body of the chamber;

wherein the disinfection part is installed on an interior wall of the body of the chamber, the method further comprising:

guiding the exhaust air having contaminants through the spiral guiding channel to the chamber;

disinfecting exhaust air by the disinfection part configured for removing the contaminants when the exhaust air passing through the body of the chamber producing a sterile air; and discharging the sterile air through the exhaust conduit.

2. The method for removing one or more contaminants from exhaust air using the disinfection device of claim 1, wherein the spiral guiding channel guides the exhaust air to the chamber and the contaminants are captured and removed by the disinfection part of the chamber.

3. The method for removing one or more contaminants from exhaust air using the disinfection device of claim 1, wherein the housing further comprises a clamping part configured for mounting the disinfection device on a drainage system.

4. The method for removing one or more contaminants from exhaust air using the disinfection device of claim 1, wherein the disinfection part further comprises a catalyst layer or a disinfectant coating.

5. A method for removing one or more contaminants from a mixture of liquid and exhaust air using a disinfection device comprising a housing, a spiral guiding channel, an exhaust conduit, and a disinfection part;

wherein the housing comprises a chamber and a top end, the chamber has a body and a reducing part, wherein the reducing part comprises an opening at a bottom end of the chamber and a floating body configured to seal the opening at the bottom end;

wherein the spiral guiding channel is external to the chamber and has an inlet and an outlet, the spiral guiding channel is adjacent to an exterior wall of the housing and connected to the outlet of the chamber;

wherein the exhaust conduit has an expandable part at one end of the exhaust conduit, and the exhaust conduit is coupled to the top end of the housing and partially extending through the body of the chamber;

wherein the disinfection part is installed on an interior wall of the body of the chamber;

the method comprising:

guiding the mixture of liquid and exhaust air through the exhaust conduit, the exhaust conduit connecting and extending into the chamber;

disinfecting the mixture of liquid and exhaust air by the disinfection part configured for removing the contaminants when the mixture of liquid and exhaust air passing through the body of the chamber producing a sterile air and a sterile liquid;

discharging the sterile air through the spiral guiding channel;

accumulating the sterile liquid at the reducing part of the chamber; and discharging the sterile liquid through the opening at the bottom end of the chamber.

6. The method for removing one or more contaminants from a mixture of liquid and exhaust air using the disinfection device of claim 5, wherein a density of the floating body is smaller than a density of the liquid.

7. The method for removing one or more contaminants from a mixture of liquid and exhaust air using the disinfection device of claim 5, wherein the exhaust conduit guides the mixture of liquid and exhaust air to the chamber and the contaminants are captured and removed by the disinfection part.

8. The method for removing one or more contaminants from a mixture of liquid and exhaust air using the disinfection device of claim 5, wherein the housing further comprises a clamping part configured for mounting the disinfection device on a drainage system.

9. The method for removing one or more contaminants from a mixture of liquid and exhaust air using the disinfection device of claim 5, wherein the disinfection part further comprises a catalyst layer.

10. The method of claim 4, wherein the disinfection part is nonluminous; and wherein the catalyst layer or the disinfectant coating does not require ultraviolet light to activate disinfection process.

11. The method of claim 9, wherein the disinfection part is nonluminous; and wherein the catalyst layer does not require ultraviolet light to activate disinfection process.

* * * * *